United States Patent [19]
Nádor et al.

[11] 4,451,473
[45] May 29, 1984

[54] 3,7-DIAZABICYCLO [3.3.1] NONANES HAVING ANTI-ARRHYTHMIC ACTIVITY

[75] Inventors: Károly Nádor; Gábor Kraiss; Katalin Sinkó; Margit Paroczai; Egon Kárpáti; László Szporny, all of Budapest, Hungary

[73] Assignee: Richter Gedeon Vegyeszeti Gyar RT, Budapest, Hungary

[21] Appl. No.: 398,801

[22] Filed: Jul. 16, 1982

[30] Foreign Application Priority Data

Jul. 20, 1981 [HU] Hungary .............................. 2112/81

[51] Int. Cl.³ .................... C07D 471/08; A61K 31/44
[52] U.S. Cl. ...................................... 424/256; 546/122
[58] Field of Search ....................... 546/122; 424/256; 542/427

[56] References Cited

PUBLICATIONS

Scheiber et al., Chem. Abs. 93:203910q, vol. 82, 124595k.
Kafka et al., Chem. Abs., vol. 82, 170823f.
Smissman et al., Chem. Abs., vol. 84, 43995e.

*Primary Examiner*—Jane T. Fan
*Attorney, Agent, or Firm*—Karl F. Ross; Herbert Dubno

[57] ABSTRACT

New bicyclic compounds of the general formula (I),

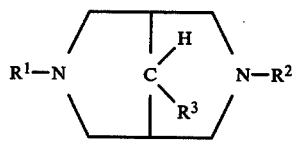

wherein
$R^1$ and $R^2$ each represent a $C_{1-6}$ alkyl group, and
$R^3$ is an etherified hydroxy group of the formula $-CR^4$, wherein $R^4$ is benzyl group, benzhydryl group or a phenyl group bearing optionally a phenyl or a trihalomethyl substituent or one or more halogen substituent(s), or
$R^3$ is an esterified hydroxy group of the formula $-O-CO-R^5$, which represents
a phenyl-($C_{1-5}$ alkyl)-carbonyloxy group,
a cinnamoyloxy group having optionally a halogen or one or more $C_{1-4}$ alkoxy substituent(s),
a benzoyloxy group having optionally a $C_{1-4}$ alkyl, phenyl or trihalomethyl substituent or one or more $C_{1-4}$ alkoxy substituent(s), one or more halo substituent(s) and/or nitro substituent,
a benzyloyloxy group,
a xanthene-9-carbonyloxy group,
an optionally substituted naphthoyloxy group, or
an acyloxy group derived from a five- or six-membered heterocyclic carboxylic acid bearing optionally a halo substituent on the ring,
are prepared by etherifying or esterifying a bicyclic compound of the general formula (II),

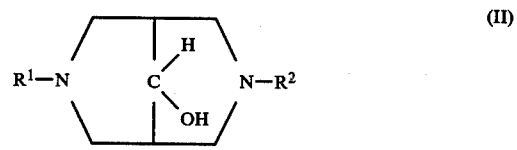

wherein $R^1$ and $R^2$ are as defined above.

The new compounds according to the invention possess anti-arrhythmic effects and can be applied to advantage in the therapy of cardiac rhythm disorders.

11 Claims, No Drawings

3,7-DIAZABICYCLO [3.3.1] NONANES HAVING ANTI-ARRHYTHMIC ACTIVITY

The invention relates to new bicyclic compounds of the formula (I),

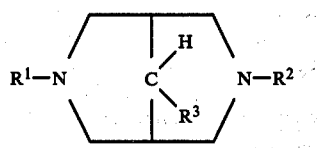

wherein
$R^1$ and $R^2$ are each $C_{1-6}$ alkyl group, and
$R^3$ is an etherified hydroxy group of the formula —$OR^4$, wherein $R^4$ is benzyl, benzhydryl or phenyl which can have a phenyl or a trihalomethyl substituent or one or more halogen substituents, or
$R^3$ is an esterified hydroxy group of the formula —O—CO—$R^5$, namely,
 a phenyl-($C_{1-5}$ alkyl)-carbonyloxy group,
 a cinnamoyloxy group which can have a halogen or one or more $C_{1-4}$ alkoxy substituents,
 a benzoyloxy group which can have a $C_{1-4}$ alkyl, phenyl or trihalomethyl group which can have a $C_{1-4}$ alkyl, phenyl or trihalomethyl substituent or one or more $C_{1-4}$ alkoxy substituents, one or more halo substituent(s) and/or a nitro substituent,
 a benzyloyloxy group,
 a xanthene-9-carbonyloxy group,
 a substituted or unsubstituted naphthoyloxy group, or
 an acyloxy group derived from a five- or six-membered heterocyclic carboxylic acid which can have a halo substituent on the ring,
and stereoisomers and pharmaceutically acceptable acid addition salts thereof. The invention also relates to a process for the preparation of these new compounds.

The new compounds of the formula (I) are biologically active and they exert particularly strong antiarrhythmic effects. The new compounds are derivatives of 3,7-diazabicyclo[3.3.1]nonane (bispidine) substituted in position 9.

The synthesis of simple compounds with bispidine skeleton, having no substituent, or having a keto group in position 9, has been described by L. J. Anet et al. [Austral J. Sci. Res. 3A, 330 (1950)] and S. Chiavarelli et al. [Gazz. Chim. Ital. 87, 109 (1957), cf. Chem. Abstr. 52, 15519d], without mentioning the biological effects of the compounds prepared.

The conformations of 3-methyl-7-alkyl-3,7-diazabicyclo[3.3.1]nonanes and the respective 9-one derivatives were analysed on the basis of NMR spectra and dipole moments by J. E. Douglass et al. [J. Org. Chem. 33, 355 (1968)] and on the basis of mass spectra by P. C. Ruenitz et al. [J. Heterocyclic Chem. 14, 423 (1977)]. The relative configuration of the carbon atom in position 9 was examined by P. Scheiber et al. [Acta Chim. Acad. Sci. Hung. 102(3), 297 (1979)] on the 9-keto and 9-hydroxy compounds being asymmetrically substituted in positions 3 and 7. However, these publications disclose the results of structural investigations only.

Bispidine compounds unsubstituted in position 9 have been reported in DE-OS No. 27 49,584 as CNS stimulating and anti-Parkinsonian agents and in DE-OS No. 27 26,571 as antiarrhythmic substances. Compositions with antiarrhythmic effects, comprising 9-unsubstituted bispidine compounds along with calcium antagonistic agents, have been disclosed in DE-OS No. 27 44,248.

9-Keto and 9-unsubstituted bispidine compounds have also been reported in the Belgian Pat. No. 830,153 (see also DE-OS 24 28,792). Of these compounds the 9-unsubstituted derivatives proved to possess antiarrhythmic effects, with a therapeutical spectrum twice as broad as that of Lidocaine.

9-Substituted 3,7-diazabicyclo[3.3.1]nonane derivatives or compounds containing such moieties have been described in the following publications:

Smissman et al. [J. Med. Chem. 19(1), 186 (1976), cf. Chem. Abstr. 84, 43995e] described the methyl ether and ethyl ester of the 9-ol compound as substances possessing analgesic effects.

Derivatives having a cycloalkylene group or a methyl and a phenyl group in position 9 have been disclosed in DE-OS No. 26 58,558 as CNS stimulating and analgesic agents.

The Belgian Pat. No. 867,086 (see also DE-OS No. 28 21,058) describes 6-aminopenicillanic acid derivatives with antiviral and antibacterial effects, which may contain, among others, N-formyl-bispidine as a substituent in position 6. In the compounds actually prepared the bispidine skeleton had no substituent in position 9.

Now it has been found that the new compounds of the formula (I), can be prepared from the respective compounds of the formula (II),

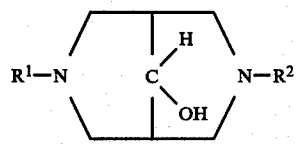

wherein $R^1$ and $R^2$ are as defined above, by etherifying or esterifying methods known per se, are particularly potent antiarrhythmic agents. This recognition is very surprising, since such an effect has not been recognized before with the known 9-substituted bispidine compounds.

The biological effects of the new compounds were examined as follows:

When examining the antiarrhythmic effects, rats were pre-treated intravenously with 1 mg/kg of aconitine to provoke disorders of cardiac rhythm [Med. Exp. (Basel) 10, 93 (1964)], thereafter the test compound was administered intravenously, and the dose required to restore the rhythm in 50% ($ED_{50}$ mg/kg) was determined.

The acute toxicities of the compounds were examined on mice under intravenous administration, and the doses which cause 50% mortality ($LD_{50}$ mg/kg) were determined. Lidocaine was used in both tests as reference.

The results of the pharmacological tests are listed in Table 1. The therapeutical indices ($ED_{50}/LD_{50}$) as well as the ratio of indices (therapeutical index of the new compound:therapeutical index of Lidocaine) are also given in the Table.

TABLE 1

| Compound | $ED_{50}$ | $LD_{50}$ | Therap. index | Ratio of indices |
|---|---|---|---|---|
| 3,7-Dimethyl-9-benzoyloxy-3,7-diazabicyclo[3.3.1]nonane | 0.08 | 9.0 | 0.009 | 39 |
| 3-Methyl-7-ethyl-9α-(4'-chloro-benzoyloxy)-3,7-diazabicyclo-[3.3.1]nonane dihydrochloride | 0.6 | 26.0 | 0.023 | 15 |

TABLE 1-continued

| Compound | ED$_{50}$ | LD$_{50}$ | Therap. index | Ratio of indices |
|---|---|---|---|---|
| 3,7-Diethyl-9-(4'-chloro-benzoyloxy)-3,7-diazabicyclo-[3.3.1]nonane dihydrochloride hydrate | 0.4 | 11.0 | 0.036 | 10 |
| 3,7-Di-n-butyl-9-(4'-chloro-benzoyloxy)-3,7-diazabicyclo-[3.3.1]nonane fumarate | 0.25 | 5.0 | 0.050 | 7 |
| 3,7-Dimethyl-9-phenoxy-3,7-diazabicyclo[3.3.1]nonane fumarate | 1.15 | 39.0 | 0.029 | 12 |
| 3,7-Dimethyl-9-(4'-chlorophenoxy)-3,7-diazabicyclo[3.3.1]-nonane fumarate | 0.9 | 52.0 | 0.017 | 21 |
| 3,7-Dimethyl-9-benzhydryloxy-3,7-diazabicyclo[3.3.1]nonane fumarate | 1.2 | 21.0 | 0.057 | 6 |
| 3-Methyl-7-ethyl-9α-(4'-chlorophenoxy)-3,7-diazabicyclo-[3.3.1]nonane dihydrochloride | 1.25 | 41.0 | 0.030 | 12 |
| 3-Methyl-7-ethyl-9α-(2'-chlorophenoxy)-3,7-diazabicyclo-[3.3.1]nonane dihydrochloride | 1.15 | 28.0 | 0.041 | 8 |
| 3-Methyl-7-ethyl-9α-(2',4'-dichlorobenzoyloxy)-3,7-diazabicyclo[3.3.1]nonane dihydrochloride | 1.1 | 20.0 | 0.055 | 6 |
| 3-Methyl-7-ethyl-9α-(4'-phenylbenzoyloxy)-3,7-diazabicyclo-[3.3.1]nonane | 1.2 | 19.5 | 0.061 | 6 |
| 3,7-Dimethyl-9-(xanthene-9'-carbonyloxy)-3,7-diazabicyclo-[3.3.1]nonane | 0.27 | 14.0 | 0.019 | 16 |
| 3,7-Dimethyl-9-(2'-naphthoyloxy)-3,7-diazabicyclo-[3.3.1]nonane bis(methane-sulfonate) | 0.11 | 17.0 | 0.006 | 58 |
| 3,7-Dimethyl-9-(3'-methoxy-4'-ethoxy-benzoyloxy)-3,7-diazabicyclo[3.3.1]nonane | 1.0 | 13.5 | 0.074 | 5 |
| Lidocaine | 10.0 | 28.5 | 0.351 | 1 |

The data of the table show that the new compounds have 5 to 58 times more favourable therapeutic effects than Lidocaine.

Similarly good results were observed in the disorder-suspending effects of the new compounds on guinea pigs pre-treated intravenously with 1 mg/kg of ouabaine to provoke cardiac rhythm disorders.

The new compounds according to the invention have no β-receptor blocking effects, whereas their local anaesthetic effects approach that of the Lidocaine. From the aspects of action mechanism it is particularly favourable that the new compounds also possess calcium antagonistic effects. The calcium antagonistic effect (pA$_2$) of 3-methyl-7-ethyl-9α-(4'-chlorobenzoyloxy)-3,7-diazabicyclo[3.3.1]nonane dihydrochloride is about the same as that of the Verapramil, a compound applied successfully in the therapy (4.33–4.6 for the former substance and 4.58–4.7 for the latter).

It was also examined how the new compounds influence the electrophysiological parameters of the heart. It was found that the new compounds have abirritant effects and increase the stimulus threshold, the impulse conduction time and the refractory period, thereby influencing the stimulus developing and impulse conducting system of the heart in a direction which is particularly favorable with respect to eliminating rhythm disorders.

The prospective therapeutical dosis of the new compounds, when applied for clinical treatment, is about 0.5–1 mg/kg under intravenous administration and about 10 mg/kg under oral administration. This amount of active agent can be administered either in a single dose or in multiple doses a day, corresponding to the disorder to be treated.

3-Methyl-7-ethyl-9α-(4'-chlorobenzoyloxy)-3,7-diazabicyclo[3.3.1]nonane dihydrochloride, a substance with a ratio of ED$_{50}$ p.o./ED$_{50}$ i.v. = 16.7, appears to be particularly suitable for oral administration.

The new compounds of the formula (I) can be prepared according to the invention so that the hydroxy group in position 9 of a compound of the formula (II), wherein R$^1$ and R$^2$ are as defined above, is esterified or etherified. More particularly, (a) when a compound of the formula (I), wherein R$^3$ is an etherified hydroxy group of the formula —OR$^4$, is to be prepared, a compound of the formula (II) or the corresponding 9-alkali metal alcoholate is reacted with a compound of the formula (III), $$R^4\text{—}X \qquad\qquad (III)$$

wherein R$^4$ is as defined above and X is halogen, or (b) when a compound of the formula (I), wherein R$^3$ is an esterified hydroxy group of the formula —O—CO—R$^5$, is to be prepared, a compound of the formula (II) is reacted with a carboxylic acid of the formula (IV), $$R^5\text{—COOH} \qquad\qquad (IV)$$

wherein the —O—CO—R$^5$ group is as defined above, or with a reactive derivative thereof, optionally in the presence of an acid binding agent, an alkali metal or another substance which catalyzes transesterification, and, if desired, the individual isomers are separated from a substance obtained as an isomeric mixture, and/or a compound of the formula (I) obtained as a free base is converted into its pharmaceutically acceptable acid addition salt, or a base of the formula (I) is liberated from its salt.

Of the starting substances having the formula (II) the derivatives in which R$^1$ and R$^2$ are the same and stand for ethyl or n-butyl group are new. These new compounds can be prepared by the catalytic hydrogenation of the respective 9-one derivatives.

With respect to the starting substances of the formula (II), the preparation of 3-methyl-7-ethyl-3,7-diazabicyclo[3.3.1]nonane-9-ol, as well as the separation of the 9α-ol and 9β-ol isomers are also new.

According to Method (a) of the invention a compound of the formula (II) is etherified with a compound of the general formula (III) on the hydroxy group in position 9 to obtain the respective ether of the formula (I). It is preferred to convert the 9-hydroxy group of the starting substance into the respective alkali metal alcoholate prior to ether formation, in order to avoid the simultaneous quaternarization of the nitrogen atoms in positions 3 and 7.

Alkali metals or hydrodes or amides thereof, such as potassium, sodium or the respective hydrides or amides, can be used as reactants for alcoholate formation. Sodium hydride is a preferred reactant. This reaction can be performed in a non-protic polar solvent, such as dimethyl formamide. The reaction proceeds easily, and can be completed by the gentle heating of the mixture.

The resulting alcoholates are reacted preferably without isolation, directly in the reaction medium where they were formed, with the halides of the formula (III). These latter reactants are used generally in a slight excess. It is preferred to utilize a fluoride derivative as etherifying agent, since it is more difficult to perform the reaction with other halo compounds of the formula (III).

The alcoholates react easily with the fluoro compounds of the formula (III). The reaction proceeds generally within 1–6 hours at 60°–110° C.

The reaction mixture is processed so that, after decomposing the alcoholates with an alcohol, the mixture is treated with an aqueous acid to transfer the basic substances into the aqueous phase, from which the non-basic substances, such as the excess of the etherifying agent of the formula (III), can be removed by extraction with a water-immiscible solvent. Thereafter the aqueous phase is treated with a base to liberate the diazabicyclic compound of the formula (I) from its salt, and this free base is extracted into an appropriate solvent. The extract is evaporated and the resulting product, if liquid, is purified by vacuum distillation or, if solid, by recrystallization. The base is obtained generally in high purity, so that it can be converted into its acid addition salt without any separate purification. The bases can be converted into their acid addition salts, preferably dihydrochlorides, dihydrobromides or fumarates, by methods known per se.

According to Method (b) of the invention a compound of the formula (II) is acylated on the hydroxy group in position 9 to obtain an ester of the formula (I).

When a free carboxylic acid of the formula (IV) is used as the acylating agent, the reaction is performed preferably in the presence of a dehydrating agent and/or an agent for activating the carboxy group.

It is more preferred, however, to use a functional derivative, such as an anhydride, a halide or a $C_{1-5}$ aliphatic ester, of a compound of the formula (IV) as acylating agent.

When a halide, preferably the chloride, of an acid of the formula (IV) is used as the acylating agent, the reaction is performed preferably in the presence of an acid binding agent. If the solvent for the reaction is a basic substance, such as a pyridine base, the excess of the solvent may also play the role of the acid binding agent. In turn, an inert organic solvent which appropriately dissolves both the starting substance and the product can also be applied as reaction medium, in combination with any known acid binding agent, such as triethyl amine. If no acid binding agent is applied in the reaction, it is recommended to use a non-protic organic solvent as reaction medium in which both the starting substance and the product are well soluble. Such solvents are the chlorinated hydrocarbons, primarily chloroform. The reaction is performed preferably at room temperature or under mild cooling, at 3°–10° C.

When a $C_{1-5}$ aliphatic ester of an acid of the formula (IV) is used as the acylating agent, it is preferred to use the acylating agent in excess and to perform the reaction in the presence of an alkali metal or another transesterification catalyst.

As catalysts e.g. alkali metals or their alcoholates, hydrides or amides can be applied. Metallic sodium proved to be a particularly suitable catalyst. Generally 0.01 to 0.1 mole of catalyst, calculated for one mole of the diazabicyclic compound, is used in the reaction. The reaction is performed in vacuo at about 80°–100° C.; under such conditions the reaction proceeds within 1–24 hours.

The reaction mixture is processed preferably as follows: The excess of the solvent is evaporated in vacuo, and, if the reaction is performed in the presence of a catalyst, the residue is treated to decompose the traces of catalyst. Thereafter the residue is taken up in an aqueous acid, the non-basic substances are removed from the mixture by extraction, the aqueous acidic phase is rendered alkaline, the free base of the formula (I) is separated from the aqueous mixture by extraction, and the extract is processed in a manner known per se. The free bases of the formula (I) are obtained generally in high purity, so that they need not be subjected to purification prior to salt formation. The bases are generally crystalline solids which can be purified, if desired, by recrystallization. If desired, the free bases can be converted into their acid addition salts, preferably dihydrochlorides, dihydrobromides, dimethanesulfates, etc., by methods known per se.

The new compounds according to the invention can be converted into pharmaceutical compositions by methods well known in the art, utilizing conventional pharmaceutical carriers, diluents and/or other additives.

The invention is elucidated in detail by the aid of the following non-limiting Examples.

EXAMPLE 1

1.08 g of sodium hydride are added to a solution of 5.0 g of 3,7-dimethyl-3,7-diazabicyclo[3.3.1]nonane-9-ol in 50 ml of dry dimethyl formamide under nitrogen atmosphere. When the spontaneous hydrogen evolution subsides, the mixture is stirred at 60° C. for 30 minutes, and then 4.8 g of fluorobenzene are added to the mixture in one portion. The mixture is maintained at 60°–100° C. for some hours. When the reaction has terminated, the mixture is diluted with 10 ml of methanol in order to decompose the excess of sodium hydride, then the mixture is acidified with 7 ml of hydrochloric acid and evaporated in vacuo. The residue is dissolved in 50 ml of water, and the solution is extracted twice with 50 ml of ether, each, in order to remove the non-basic substances. Potassium carbonate is added to the aqueous phase until an oily substance separates, which is extracted thrice with 50 ml of diethyl ether, each. The etheral extracts are combined, dried over magnesium sulfate, filtered, the filtrate is evaporated, and the free base, obtained as a residue, is converted into its fumarate. The salt is obtained with a yield of 71.9%, related to the base.

The resulting 3,7-dimethyl-9-phenoxy-3,7-diazabicyclo[3.3.1]nonane fumarate melts at 196°–197° C. after recrystallization from a mixture of ethanol and diisopropyl ether. The base is a colorless oily substance; b.p.: 121°–122° C./10 Pa, $n_D^{20} = 1.5472$.

The aminoalcohol used as starting substance is prepared from 3,7-dimethyl-3,7-diazabicyclo[3.3.1]nonane-9-one, a known substance, by catalytic hydrogenation. The 9-ol compound melts at 130°–131° C. after recrystallization from hexane.

EXAMPLE 2

1 molar equivalent of 3,7-dimethyl-3,7-diazabicyclo[3.3.1]nonane-9-ol is reacted with 1.5 molar equivalents of the respective aryl fluoride as described in Example 1 to obtain the following compounds:

(a) 3,7-Dimethyl-9-(4'-chlorophenoxy)-3,7-diazabicyclo[3.3.1]nonane fumarate; yield: 51%, m.p.: 211° C.

(after recrystallization from methanol and diisopropyl ether).

(b) 3,7-Dimethyl-9-(3'-trifluoromethyl-phenoxy)-3,7-diazabicyclo[3.3.1]nonane dihydrochloride; yield: 75.5%, m.p.: 196° C. (after recrystallization from n-butanol).

EXAMPLE 3

10 g of 3,7-dimethyl-3,7-diazabicyclo[3.3.1]nonane-9-ol are reacted with 24.7 g of benzhydryl bromide as described in Example 1. The product is converted into its fumarate, the salt is dissolved in methanol, and precipitated with methylethyl-ketone. 3,7-Dimethyl-9-benzhydryloxy-3,7-diazabicyclo[3.3.1]nonane fumarate is obtained with a yield of 50%; m.p.: 200°–201° C.

EXAMPLE 4

18.3 g of 3,7-dimethyl-3,7-diazabicyclo[3.3.1]nonane-9-ol are reacted with 13.5 g of benzyl chloride for 4 hours at room temperature as described in Example 1. 9 g (32.3%) of 3,7-dimethyl-9-benzyloxy-3,7-diazabicyclo[3.3.1]nonane are obtained; b.p.: 137°–148° C./10 Pa. The free base rapidly crystallizes upon standing; m.p.: 70°–75° C.

The base is converted into its fumarate in a manner known per se. The salt melts at 145°–146° C. after recrystallization from ethanol.

EXAMPLE 5

10 g of 3-methyl-7-ethyl-3,7-diazabicyclo[3.3.1]nonane-9α-ol are reacted, in a solution formed with 50 ml of dry dimethyl formamide, with 8.93 g of fluorobenzene as described in Example 1. The product is purified by vacuum distillation. 3-Methyl-7-ethyl-9α-phenoxy-3,7-diazabicyclo[3.3.1]nonane is obtained with a yield of 69.3%; b.p.: 132°–134° C./18 Pa, $n_D^{20}=1.5412$.

The dihydrochloride of the above base melts at 230°–231° C. after recrystallization from a mixture of isopropanol and methyl-ethyl-ketone.

3-Methyl-7-ethyl-3,7-diazabicyclo[3.3.1]nonane-9-ol, the starting substance of the above reaction, is prepared as follows:

3-Methyl-7-ethyl-3,7-diazabicyclo[3.3.1]nonane-9-one is prepared first from 1-methyl-4-piperidone, paraformaldehyde and ethyl amine according to the method of J. E. Douglass et al. [J. Org. Chem. 33, 355 (1968)]. The compound is obtained with a yield of 92.3%; b.p.: 96°–97° C./3 Pa, $n_D^{20}=1.4971$.

18.2 g of 3-methyl-7-ethyl-3,7-diazabicyclo[3.3.1]nonane-9-one are dissolved in 150 ml of ethanol, and the solution is hydrogenated for about 4 hours at a starting pressure of 4 MPa in the presence of 1 g of platinum(IV) oxide catalyst. The reaction mixture contains the two possible isomers in a ratio of 50:50. The isomer wherein the hydroxy group in position 9 is on the side of the N-ethyl group is termed as α-isomer, whereas that in which the hydroxy group in position 9 is on the side of the N-methyl group is termed as β isomer.

The isomeric mixture is treated with alcoholic hydrochloric acid in isopropanol medium. The α isomer, which precipitates as the dihydrochloride, is separated and recrystallized twice from isopropanol. The salt, weighing 7.7 g, is obtained with a yield of 60%; m.p.: 250° C. (under decomposition).

The base liberated from this salt is a colourless crystalline substance melting at 88°–89° C. The $^1$H NMR spectral data which prove the structure of the isomer are reported by P. Scheiber and K. Nádor [Acta Chim. Acad. Sci. Hung. 102, 297 (1979)]. When subjected to thin layer chromatography on Kieselgel 60 adsorbent, utilizing 9:1 to 7:3 mixtures of ethanol and 25% aqueous ammonia as solvent, the compound proved to be uniform.

The mother liquors obtained at the crystallization of the α isomer are combined and evaporated, and the resulting salt, weighing 18 g, is dissolved in 50 ml of water. The solution is saturated with potassium carbonate, and the liberated base is extracted five times with 60 ml of chloroform, each. The chloroform solutions are combined, dried over magnesium sulfate, filtered, and the filtrate is evaporated. The residue is crystallized from petroleum ether (b.p.: 120° C.) to obtain stereochemically pure 3-methyl-7-ethyl-3,7-diazabicyclo[3.3.1]nonane-9β-ol as a colourless, crystalline substance melting at 98°–99° C. Yield: 30% (2.7 g) after four crystallization steps.

The unity of the β isomer is proved by thin layer chromatography, the steric position of the 9β-hydroxy group is confirmed by $^1$H NMR spectroscopy as described above in connection with the α isomer.

EXAMPLE 6

3-Methyl-7-ethyl-3,7-dizabicyclo[3.3.1]nonane-9α-ol, prepared as described in Example 5, is converted into the following 9α-aryloxy derivatives according to the method of Example 1:

(a) 3-Methyl-7-ethyl-9α-(3'-trifluoromethyl-phenozy)-3,7-diazabicyclo[3.3.1]nonane dihydrochloride; m.p.: 160°–161° C. (from ethanol, acetone and ether), yield: 62.5%.

(b) 3-Methyl-7-ethyl-9α-(4'-chlorophenoxy)-3,7-diazabicyclo[3.3.1]nonane dihydrochloride; m.p.: 139°–141° C. (from isopropanol and ether), yield: 51.5%.

(c) 3-Methyl-7-ethyl-9α-(3'-chlorophenoxy)-3,7-diazabicyclo[3.3.1]nonane dihydrochloride; m.p.: 209°–210° C. (from ethanol, acetone and ether), yield: 76.9%.

(d) 3-Methyl-7-ethyl-9α-(2'-chlorophenoxy)-3,7-diazabicyclo[3.3.1]nonane dihydrochloride; m.p.: 241°–242° C. (from ethanol, acetone and ether), yield: 40%.

(e) 3-Methyl-7-ethyl-9α-(4'-phenylphenoxy)-3,7-diazabicyclo[3.3.1]nonane; m.p.: 91°–92° C. (after recrystallization from n-hexane), yield: 35%.

EXAMPLE 7

3-Methyl-7-ethyl-3,7-diazabicyclo[3.3.1]nonane-9β-ol, prepared as described in Example 5, is reacted with 3-trifluoromethyl-fluorobenzene as described in Example 1 to obtain 3-methyl-7-ethyl-9β-(3'-trifluoromethyl-phenoxy)-3,7-diazabicyclo[3.3.1]nonane base with a yield of 34.5%; b.p.: 121°–122° C./9 Pa, $n^{20}=1.3605$. The dihydrochloride salt is a colorless, crystalline substance melting at 163°–164° C. after recrystallization from isopropanol.

EXAMPLE 8

10 g of 3,7-dimethyl-3,7-diazabicyclo[3.3.1]nonane-9-ol are dissolved in 50 ml of dry pyridine, and a solution of 11.24 g of benzoyl chloride in 50 ml of dry pyridine is added dropwise, within 30 minutes, to the solution stirred at 5°–10° C. Thereafter the reaction mixture is stirred at room temperature for 3 hours, and the bulk of pyridine is distilled off under vacuo. The residue is taken up in 50 ml of water, the mixture is acidified with 20 ml of concentrated aqueous hydrochloric acid, and the mixture is extracted thrice with 50 ml of ether, each, in order to remove the non-basic substances. The aqueous phase is rendered alkaline with potassium carbonate and extracted thrice with 50 ml of chloroform, each. The chloroform solutions are combined, dried over magnesium sulfate, filtered, and the filtrate is evaporated. The residue is crystallized from n-hexane. 3,7-Dimethyl-9-benzoyloxy-3,7-diazabicyclo[3.3.1]nonane is obtained with a yield of 42.5%; m.p.: 100°–102° C.

The base is converted into its dihydrochloride in a manner known per se. The crystalline salt melts at 260° C. after recrystallization from isopropanol.

EXAMPLE 9

3,7-Dimethyl-3,7-diazabicyclo[3.3.1]nonane-9-ol is reacted with the appropriate acyl halides as described in Example 8 to obtain the following compounds:

(a) When 4-nitrobenzoyl chloride is utilized as reactant, 3,7-dimethyl-9-(4'-nitrobenzoyloxy)-3,7-diazabicyclo[3.3.1]nonane is obtained with a yield of 80.6%. The product melts at 150° C. after recrystallization from glycol dimethyl ether.

The dihydrochloride of the above compound separates as a hemihydrate after recrystallization from methanol; m.p.: 272° C.

(b) When 4-chlorocinnamoyl chloride is utilized as reactant, 3,7-dimethyl-9-(4'-chlorocinnamoyloxy)-3,7-diazabicyclo[3.3.1]nonane is obtained with a yield of 75.3%. The product melts at 111°–112° C. after recrystallization from diisopropyl ether.

(c) When 4-methoxycinnamoyl chloride is used as reactant, 3,7-dimethyl-9-(4'-methoxy-cinnamoyloxy)-3,7-diazabicyclo[3.3.1]nonane is obtained with a yield of 87.2%. The resulting thick, yellow oil is converted directly into the dihydrochloride. The salt melts at 230° C. under decomposition after recrystallization from alcohol.

(d) When 3,4,5-trimethoxy-cinnamoyl chloride is used as reactant, 3,7-dimethyl-9-(3',4',5'-trimethoxy-cinnamoyloxy)-3,7-diazabicyclo[3.3.1]nonane is obtained with a yield of 61.5%. The product melts at 130° C. after crystallization from diisopropyl ether. The dihydrochloride of the base melts at 248° C. under decomposition after recrystallization from aqueous alcohol.

EXAMPLE 10

6 g of 3-methyl-7-ethyl-3,7-diazabicyclo[3.3.1]nonane-9α-ol are reacted with 9.16 g of benzoyl chloride as described in Example 8 to obtain 3-methyl-7-ethyl-9α-benzoyloxy-3,7-diazabicyclo[3.3.1]nonane with a yield of 60.7%. The oily product boils at 175°–178° C./1.2 kPa; $n_D^{20} = 1.5275$. The dihydrochloride monohydrate of the free base melts at 236°–237° C. after recrystallization from isopropanol.

EXAMPLE 11

The following 3-methyl-7-ethyl-9α-aroyloxy-3,7-diazabicyclo[3.3.1]nonane derivatives are prepared from the appropriate starting substances according to the method of the previous examples:

(a) 3-Methyl-7-ethyl-9α-(2',4'-dichloro-benzoyloxy)-3,7-diazabicyclo[3.3.1]nonane dihydrochloride; m.p.: 105°–107° C. (after recrystallization from a mixture of ethanol and ether), yield: 48.1%.

(b) 3-Methyl-7-ethyl-9α-(4'-chloro-benzoyloxy)-3,7-diazabicyclo[3.3.1]nonane dihydrochloride; m.p.: 140°–142° C. (after recrystallization from a mixture of ethanol and ether), yield: 48.2%.

(c) 3-Methyl-7-ethyl-9α-(4'-phenyl-benzoyloxy)-3,7-diazabicyclo[3.3.1]nonane; m.p.: 91°–92° C. (after recrystallization from n-hexane), yield: 50%. The dihydrochloride melts at 183°–185° C. after recrystallization from a mixture of ethanol and ether.

EXAMPLE 12

3-Methyl-7-ethyl-3,7-diazabicyclo[3.3.1]nonane-9β-ol is reacted with 4-chloro-benzoyl chloride as described in Example 8 to obtain 3-methyl-7-ethyl-9β-(4'-chloro-benzoyloxy)-3,7-diazabicyclo[3.3.1]nonane with a yield of 70%. The base melts at 66°–67° C. after crystallization from petroleum ether (b.p.: 120° C.).

The dihydrochloride of the above base, prepared in a manner known per se, is a colorless crystalline substance melting at 175° C. after recrystallization from isopropanol.

EXAMPLE 13

9.9 g of 3,7-diethyl-3,7-diazabicyclo[3.3.1]nonane-9-ol are reacted with 4-chloro-benzoyl chloride as described in Example 8 to obtain 3,7-diethyl-9-(4'-chloro-benzoyloxy)-3,7-diazabicyclo[3.3.1]nonane dihydrochloride monohydrate with a yield of 53.8%; m.p.: 116°–120° C.

The starting substance can be prepared as follows:
1-Ethyl-4-piperidone is reacted with paraformaldehyde and ethyl amine to obtain 3,7-diethyl-3,7-diazabicyclo[3.3.1]nonane-9-one with a yield of 68%; b.p.: 87° C./1.3 Pa, $n_D^{20} = 1.4935$. 76 g of the resulting substance are dissolved in 300 ml of dry alcohol, 0.6 g of platinum(IV) oxide (Adams catalyst) are added, and the mixture is hydrogenated under a starting pressure of 7 MPa for about 7 hours. The catalyst is filtered off, the filtrate is evaporated, and the residue is recrystallized from heptane. 54 g (71%) of 3,7-diethyl-3,7-diazabicyclo[3.3.1]nonane-9-ol are obtained; m.p.: 61.5° C.

EXAMPLE 14

10.18 g of 3,7-di-n-butyl-3,7-diazabicyclo[3.3.1]nonane-9-ol are reacted with 7.7 g of 4-chloro-benzoyl chloride as described in Example 8 to obtain 3,7-di-n-butyl-9-(4'-chlorobenzoyloxy)-3,7-diazabicyclo[3.3.1]nonane, which is converted into its fumarate. The salt, melting at 180°–181° C., is obtained with a yield of 57.5%.

The starting substance is prepared from 3,7-di-n-butyl-3,7-diazabicyclo[3.3.1]nonane-9-one (b.p.: 123° C./7 Pa, $n_D^{20}$ 1.4863) by the catalytic reduction method described in Example 13. The resulting 3,7-di-n-butyl-3,7-diazabicyclo[3.3.1]nonane-9-ol is recrystallized from petroleum ether (b.p.: 120° C.) and then subjected to sublimation in vacuo. The colourless, crystalline substance melts at 31°–32° C.

EXAMPLE 15

10 g of 3,7-dimethyl-3,7-diazabicyclo[3.3.1]nonane-9-ol are reacted with 19.57 g of xanthene-9-carbonyl chloride as described in Example 8 to obtain 3,7-dimethyl-9-(xanthene-9'-carbonyloxy)-3,7-diazabicyclo[3.3.1]nonane with a yield of 58.3%. The free base melts at 108° C. after recrystallization from n-hexane, and the respective fumarate melts at 191°–193° C. after recrystallization from a mixture of ethanol and ether.

EXAMPLE 16

13.3 g of 2-naphthoyl chloride are added to a solution of 8.5 g of 3,7-dimethyl-3,7-diazabicyclo[3.3.1]nonane-9-ol in 100 ml of chloroform at a temperature below 20° C., and then the reaction mixture is allowed to stand at room temperature for one hour. The chloroform solution is evaporated in vacuo, and the residue is taken up in 100 ml of water. The aqueous solution is acidified with 10 ml of hydrochloric acid and extracted then twice with 50 ml of ether, each. The aqueous phase is rendered alkaline with potassium carbonate, and the liberated base is extracted thrice with 50 ml of chloroform, each. The chloroform extracts are combined, dried over magnesium sulfate, filtered, and the filtrate is evaporated. The crystalline residue melts at 76°–78° C. after recrystallization from 2-butanone; yield: 99%. The resulting 3,7-dimethyl-9-(2'-naphthoyloxy)-3,7-diazabicyclo[3.3.1]nonane is converted into its di(methanesulfonate) in a manner known per se. The salt melts at 212° C. after recrystallization from ethanol.

EXAMPLE 17

3,7-Dimethyl-3,7-diazabicyclo[3.3.1]nonane-9-ol is reacted with the appropriate acylating agents as described in Example 16 to obtain the following compounds:
(a) 3,7-Dimethyl-9-(4'-methyl-benzoyloxy)-3,7-diazabicyclo[3.3.1]nonane; yield: 83%, m.p.: 59°–60° C. (after sublimation in vacuo). The dihydrobromide, prepared in a manner known per se, melts at 231°–233° C. after recrystallization from methanol.
(b) 3,7-Dimethyl-9-(4'-ethyl-benzoyloxy)-3,7-diazabicyclo[3.3.1]nonane; yield: 90%, m.p.: 62°–63° C. (after sublimation in vacuo). The dihydrobromide, prepared in a manner known per se, melts at 233°–234° C. under decomposition after recrystallization from ethanol.
(c) 3,7-Dimethyl-9-(4'-chloro-benzoyloxy)-3,7-diazabicyclo[3.3.1]nonane; yield: 93%, m.p.: 87°–89° C. (after sublimation in vacuo). The dihydrobromide, prepared in a manner known per se, melts at 260° C. under decomposition after recrystallization from aqueous acetone.
(d) 3,7-Dimethyl-9-(2'-chloro-4'-nitro-benzoyloxy)-3,7-diazabicyclo[3.3.1]nonane; yield: 73%, m.p.: 116°–117° C. (after recrystallization from acetone). The dihydrobromide, prepared in a manner known per se, melts at 237°–238° C. under decomposition after recrystallization from aqueous acetone.
(e) 3,7-Dimethyl-9-(3'-methoxy-4'-ethoxy-benzoyloxy)-3,7-diazabicyclo[3.3.1]nonane; yield: 93%, m.p.: 72°–73° C. (after sublimation in vacuo). The dihydrobromide, prepared in a manner known per se, melts at 178°–180° C. under decomposition after recrystallization from ethanol.
(f) 3,7-Dimethyl-9-(2'-furoyloxy)-3,7-diazabicyclo[3.3.1]nonane; yield: 71.9%, m.p.: 131°–132° C. (after recrystallization from acetone). The dihydrobromide, prepared in a manner known per se, melts at 239°–241° C. under decomposition after recrystallization from methanol.
(g) 3,7-Dimethyl-9-(2'-chloro-nicotinoyloxy)-3,7-diazabicyclo[3.3.1]nonane; yield: 85%, m.p.: 123°–125° C. (after recrystallization from methylethyl-ketone). The dihydrobromide, prepared in a manner known per se, melts at 260° C. under decomposition after recrystallization from aqueous methanol.
(h) 3,7-Dimethyl-9-(2'-thenoyloxy)-3,7-diazabicyclo[3.3.1]nonane; yield: 83%, m.p.: 96°–97° C. The dihydrobromide, prepared in a manner known per se, melts at 260°–262° C. under decomposition after recrystallization from methanol.

EXAMPLE 18

0.3 g of metallic sodium are added, as small chips, to a mixture of 8 g of 3,7-dimethyl-3,7-diazabicyclo[3.3.1]nonane-9-ol and 22 g (an excess of 185%) of phenylacetic acid ethyl ester. The reaction mixture is maintained at a water bath heated to 90° C. for 6 hours under a vacuum of 2 kPa. The pressure is then adjusted to atmospheric, the reaction mixture is diluted with 50 ml of ether, and the basic substances are extracted twice with 75 ml of 10% aqueous hydrochloric acid solution, each. The aqueous phases are combined, rendered alkaline with potassium carbonate, and the product, which separates as an oil, is extracted thrice with 50 ml of chloroform, each. The chloroform extracts are combined, dried over magnesium sulfate, filtered, the solvent is evaporated in vacuo, and the residue is distilled in vacuo.

3,7-Dimethyl-9-phenylacetoxy-3,7-diazabicyclo[3.3.1]nonane is obtained with a yield of 88.5%; b.p.: 168° C./20 Pa, $n_D^{25} = 1.5310$. The dihydrobromide, prepared in a manner known per se, melts at 230° C. after recrystallization from methanol.

EXAMPLE 19

3,7-Dimethyl-3,7-diazabicyclo[3.3.1]nonane-9-ol is reacted with a 100% excess of the appropriate carboxylic acid ester as described in Example 18 to obtain the following compounds:
(a) 3,7-Dimethyl-9-benzoyloxy-3,7-diazabicyclo[3.3.1]nonane; yield: 57.8%, m.p.: 119° C. (after crystallization from diisopropyl ether). The fumarate melts at 205° C. after recrystallization from a mixture of methanol and ethanol.
(b) 3,7-Dimethyl-9-nicotinoyloxy-3,7-diazabicyclo[3.3.1]nonane; b.p.: 183° C./140 Pa, m.p.: 70°–75° C. The trihydrobromide, prepared in a manner known per se, melts at 262° C. after recrystallization from methanol.

What we claim is:
1. A bicyclic compound of the formula (I)

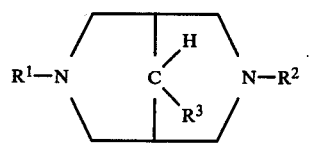

wherein
$R^1$ and $R^2$ are each $C_{1-6}$ alkyl and
$R^3$ is an etherified hydroxy group of the formula —$OR^4$, wherein
$R^4$ is benzyl, benzhydryl or phenyl which can have a phenyl or a trihalomethyl substituent or a halogen substituent, or
$R^3$ is an esterified hydroxy group of the formula —O—CO—$R^5$ selected from the group which consists of:
a phenyl-($C_{1-5}$ alkyl)-carbonyloxy group,
a cinnamoyloxy group which can have a halogen or one to three $C_{1-4}$ alkoxy substituents, a benzoyloxy group which can have a $C_{1-4}$ alkyl, phenyl or trihalomethyl substituent or one or two $C_{1-4}$ alkoxy substituents, one or two halo substituents and/or a nitro substituent, a benzyloyloxy group, a xanthene-9-carbonyloxy group, a naphthoyloxy group, or a thenoyloxy, nicotinoyloxy, or furoyloxy group each of which can have a halo substituent on the ring, or a stereoisomer or a pharmaceutically acceptable acid addition salt thereof.

2. A compound as defined in claim 1 wherein $R^1$ and $R^2$ are the same and stand for ethyl or n-butyl groups.

3. 3,7-dimethyl-9-phenoxy-3,7-diazabicyclo[3.3.1]nonane or a pharmaceutically acceptable acid addition salt thereof as defined in claim 1.

4. 3,7-dimethyl-9-(4'-chlorophenoxy)-3,7-diazabicyclo[3.3.1]nonane or a pharmaceutically acceptable acid addition salt thereof as defined in claim 1.

5. 3-methyl-7-ethyl-9α-(4'-chlorophenoxy)-3,7-diazabicyclo[3.3.1]nonane or a pharmaceutically acceptable acid addition salt thereof as defined in claim 1.

6. 3,7-dimethyl-9-benzoyloxy-3,7-diazabicyclo[3.3.1]nonane or a pharmaceutically acceptable acid addition salt thereof as defined in claim 1.

7. 3-methyl-7-ethyl-9α-(4'-chlorobenzoyloxy)-3,7-diazabicyclo[3.3.1]nonane or a pharmaceutically acceptable acid addition salt thereof as defined in claim 1.

8. 3,7-dimethyl-9-(xanthene-9'-carbonyloxy)-3,7-diazabicyclo[3.3.1]nonane or a pharmaceutically acceptable acid addition salt thereof as defined in claim 1.

9. 3,7-dimethyl-9-(2'-naphthoyloxy)-3,7-diazabicyclo[3.3.1]nonane or a pharmaceutically acceptable acid addition salt thereof as defined in claim 1.

10. An antiarrhythmic composition containing as active agent a pharmaceutically effective amount of a compound as defined in claim 1 or a stereoisomer or a pharmaceutically acceptable acid addition salt thereof and a pharmaceutical carrier.

11. An antiarrhythmic method of treatment which comprises administering a pharmaceutically effective amount of a compound or pharmaceutically acceptable acid addition salt thereof, as defined in claim 1 to a subject suffering from arrhythmia.

* * * * *